(12) United States Patent
Thompson

(10) Patent No.: US 6,648,823 B2
(45) Date of Patent: Nov. 18, 2003

(54) METHOD AND SYSTEM OF FOLLOW-UP SUPPORT FOR A MEDICAL DEVICE

(75) Inventor: David L. Thompson, Andover, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/919,519

(22) Filed: Jul. 31, 2001

(65) Prior Publication Data
US 2003/0028082 A1 Feb. 6, 2003

(51) Int. Cl.⁷ .............................. A61B 5/00; A61N 1/378
(52) U.S. Cl. .................... 600/300; 607/29; 607/60; 128/903
(58) Field of Search .................... 607/27, 29, 30, 607/59, 60; 714/47; 600/300, 301; 128/903, 904; 604/891.1, 502

(56) References Cited

U.S. PATENT DOCUMENTS

| | | | |
|---|---|---|---|
| 4,494,950 A | 1/1985 | Fischell | 604/66 |
| 4,606,350 A | 8/1986 | Frost | 128/419 PG |
| 4,886,064 A | 12/1989 | Strandberg | 128/419 PG |
| 4,979,507 A | 12/1990 | Heinz et al. | 128/419 PG |
| 5,137,020 A | 8/1992 | Wayne et al. | 128/419 PS |
| 5,309,919 A | 5/1994 | Snell et al. | 128/697 |
| 5,330,513 A | 7/1994 | Nichols et al. | 607/32 |
| 5,345,362 A | 9/1994 | Winkler | 361/381 |
| 5,391,193 A | 2/1995 | Thompson | 607/29 |
| 5,620,474 A | 4/1997 | Koopman | 607/29 |
| 5,697,959 A | 12/1997 | Poore | |
| 5,720,770 A * | 2/1998 | Nappholz et al. | 128/903 |
| 5,800,473 A * | 9/1998 | Faisandier | 607/59 |
| 5,855,609 A | 1/1999 | Knapp | 623/11 |
| 6,083,248 A | 7/2000 | Thompson | 607/30 |
| 6,108,579 A * | 8/2000 | Snell et al. | 607/29 |
| 6,185,461 B1 * | 2/2001 | Er | 607/27 |
| 6,247,145 B1 * | 6/2001 | Witteried | 714/47 |
| 6,249,705 B1 | 6/2001 | Snell | |
| 6,363,282 B1 * | 3/2002 | Nichols et al. | 607/30 |

FOREIGN PATENT DOCUMENTS

| | | |
|---|---|---|
| EP | 1 057 448 A1 | 12/2000 |
| WO | WO 99/14882 | 3/1999 |
| WO | WO 00/54237 | 9/2000 |
| WO | WO 01/49368 | 7/2001 |

* cited by examiner

Primary Examiner—Eric F. Winakur
Assistant Examiner—David J. McCrosky
(74) Attorney, Agent, or Firm—Girma Wolde-Michael; Michael C. Soldner (57) ABSTRACT

A method and structure for notifying clinicians with patients with implantable medical devices (IMDs), about recalls and upgrades, therapy improvements, longevity estimates/improvements, and follow-up frequency recommendations is implemented in an interactive preferably wireless communications system involving a preferably web-enabled remote expert station. Either the clinician or the patient may initiate and access the remote expert station. During such communications, the patient's IMDs are evaluated against a first database comprising patient data and a second database comprising statistical, survivability, probability projections. The patient or the clinician may also access a database containing patient-specific information including other device information. If one or more of the patient's IMDs matches with a recalled or an up-gradable unit such message is posted to the clinician and the patient. Remedial action is taken, by replacing the unit, upgrading/reprogramming the unit, adjusting the patient's follow-up timing to thereby ensure effective and safe therapy and clinical care.

7 Claims, 7 Drawing Sheets

METHOD AND SYSTEM OF FOLLOW-UP SUPPORT FOR A MEDICAL DEVICE

THE FIELD OF THE INVENTION

The present invention relates to medical device systems. Specifically, the invention pertains to a remote bi-directional communications with one or more programmers and medical units, or related controls that are associated with implantable medical devices (IMDs). More specifically, the invention relates to a system to aid in the initial implant and subsequent follow-up of IMDs. The invention utilizes a highly integrated system and method of bi-directional telecommunications between a web-based expert data center and a medical device, utilizing various types of network platforms and architecture, to inform patients and clinicians upon connection with the expert data center about recalls or alerts and recommend courses of action relating to the selection of programmable parameters and the course of treatment/follow-up of an IMD.

BACKGROUND OF THE INVENTION

A technology-based health care system that fully integrates the technical and social aspects of patient care and therapy should be able to flawlessly connect the client with care providers irrespective of separation distance or location of the participants. While clinicians will continue to treat patients in accordance with accepted modern medical practice, developments in communications technology are making it ever more possible to provide a seamless system of remote patient diagnostics, care and medical services in a time and place independent manner.

Prior art methods of clinical services are generally limited to in-hospital operations. For example, if a physician needs to review the performance parameters of an implantable device in a patient, it is likely that the patient has to go to the clinic. Further, if the medical conditions of a patient with an implantable device warrant a continuous monitoring or adjustment of the device, the patient would have to stay in a hospital indefinitely. Such a continued treatment plan poses both economic and social problems. Under the exemplary scenario, as the segment of the population with implanted medical devices increases many more hospitals/clinics including service personnel will be needed to provide in-hospital service for the patients, thus escalating the cost of healthcare. Additionally the patients will be unduly restricted and inconvenienced by the need to either stay in the hospital or make very frequent visits to a clinic.

Yet another condition of the prior art practice requires that a patient visit a clinic center for occasional retrieval of data from the implanted device to assess the operations of the device and gather patient history for both clinical and research purposes. Such data is acquired by having the patient in a hospital/clinic to down load the stored data from the implantable medical device. Depending on the frequency of data collection this procedure may pose serious difficulty and inconvenience for patients who live in rural areas or have limited mobility. Similarly, in the event a need arises to upgrade the software of an implantable medical device, the patient will be required to come into the clinic or hospital to have the upgrade installed. Further, in medical practice it is an industry-wide standard to keep an accurate record of past and contemporaneous procedures relating to an IMD uplink with, for example, a programmer. It is required that the report contains the identification of all the medical devices involved in any interactive procedure. Specifically, all peripheral and major devices that are used in down linking to the IMD need to be reported. Currently, such procedures are manually reported and require an operator or a medical person to diligently enter data during each procedure. One of the limitations of the reporting procedure is the fact that it is error prone and requires rechecking of the data to verify accuracy. Further, under present medical device databases, there is no well-defined interactive system that enables patients and clinicians to be aware of recalled or upgradeable units/components for IMDs.

IMDs, programmers and related medical devices are distributed throughout the world. Further, the number of people with implanted medical devices has been increasing over the last few years. Thus, it is important to provide a broadcast system for recalled devices to ensure the safety of these globally distributed medical devices. Specifically, at current global distribution levels a web-enabled alert system of notification is a vital and necessary tool to promote safe therapy and clinical care worldwide.

A further limitation of the prior art relates to the management of multiple medical devices in a single patient. Advances in modern patient therapy and treatment have made it possible to implant a number of devices in a patient. For example, IMDs such as a defibrillator or a pacer, a neural implant, a drug pump, a separate physiologic monitor and various other IMDs may be implanted in a single patient. To successfully manage the operations and assess the performance of each device in a patient with multi-implants requires a continuous update and monitoring of the devices. Further, it may be preferred to have an operable communication between the various implants to provide a coordinated clinical therapy to the patient. Thus, there is a need to monitor the IMDs including the programmer on a regular, if not a continuous, basis to ensure optimal patient care.

Accordingly it is vital to have a programmer unit that would connect to a remote expert data center, a remote web-based data center or a remote data center, all these terms being alternate equivalents as used herein, to provide access to a database of recalled devices. More specifically, it is most desirable to provide globally distributed patients and their doctors information about recalled IMDs and those needing an upgrade consistent with standards set by the manufacturers of the IMDs.

The proliferation of patients with multi-implant medical devices worldwide has made it imperative to provide remote services to the IMDs and timely clinical care to the patient. Frequent use of programmers to communicate with the IMDs and provide various remote services, consistent with co-pending applications titled "Apparatus and Method for Remote Troubleshooting, Maintenance and Upgrade of Implantable Device Systems," filed on Oct. 26, 1999, Ser. No. 09/426,741; "Tactile Feedback for Indicating Validity of Communication Link with an Implantable Medical Device," filed Oct. 29, 1999, Ser. No. 09/430,708; "Apparatus and Method for Automated Invoicing of Medical Device Systems," filed Oct. 29, 1999, Ser. No. 09/430,208; "Apparatus and Method for Remote Self-Identification of Components in Medical Device Systems," filed Oct. 29, 1999, Ser. No. 09/429,956; "Apparatus and Method to Automate Remote Software Updates of Medical Device Systems," filed Oct. 29, 1999, Ser. No. 09/429,960; "Method and Apparatus to Secure Data Transfer From Medical Device Systems," filed Nov. 2, 1999, Ser. No. 09/431,881; "Implantable Medical Device Programming Apparatus Having An Auxiliary Component Storage Compartment," filed Nov. 4, 1999, Ser. No. 09/433,477; "System of Notification of Recalled Components for a Medical Device," filed Dec. 29, 1999, Ser. No. 09/474,694; which are all incorporated by reference herein in their entirety, has become an important aspect of patient care. Thus, in light of the referenced disclosures, remote access to a data bank of recalled devices both consisting of Medtronic, Inc. and products made by other manufacturers, is a vital step in providing efficient therapy and clinical care to the patient.

The prior art provides various types of remote sensing and communications with IMDs. Stranberg in U.S. Pat. No. 4,886,064, issued Dec. 12, 1989, for example, discloses one such system. In this disclosure, body activity sensors, such as temperature, motion, respiration and /or blood oxygen sensors, are positioned in a patient's body outside a pacer capsule. The sensors wirelessly transmit body activity signals, which are processed by circuitry in the heart pacer. The heart pacing functions are influenced by the processed signals. The signal transmission is a two-way network and allows the sensors to receive control signals for altering the sensor characteristics.

One of the many limitations of Stranberg is the fact that although there is corporeal two-way communications between the implantable medical devices, and the functional response of the heart pacer is processed in the pacer after collecting input from the other sensors, the processor is not remotely programmable. Specifically, the system does not lend itself to web-based communications because the processor/programmer is internally located in the patient forming an integral part of the heart pacer.

Yet another prior art reference provides a multi-module medication delivery system as disclosed by Fischell in U.S. Pat. No. 4,494,950 issued Jan. 22, 1985. The disclosure relates to a system consisting a multiplicity of separate modules that collectively perform a useful biomedical purpose. The modules communicate with each other without the use of interconnecting wires. All the modules may be installed intracorporeal or mounted extracorporeal to the patient. In the alternate, some modules may be intracorporeal with others being extracorporeal. Signals are sent from one module to the other by electromagnetic waves. Physiologic sensor measurements sent from a first module cause a second module to perform some function in a closed loop manner. One extracorporeal module can provide electrical power to an intracorporeal module to operate a data transfer unit for transferring data to the external module.

The Fischell disclosure provides modular communication and cooperation between various medication delivery systems. However, the disclosure does not provide an external programmer with remote sensing, remote data management and maintenance of the modules. Further, the system does neither teach nor disclose the notification/recommendation scheme contemplated by the present invention.

An additional example of prior art practice includes a packet-based telemedicine system for communicating information between central monitoring stations and a remote patient monitoring station disclosed in Peifer, WO 99/14882 published Mar. 25, 1999. The disclosure relates to a packet-based telemedicine system for communicating video, voice and medical data between a central monitoring station and a patient that is remotely located with respect to the central monitoring station. The patient monitoring station obtains digital video, voice and medical measurement data from a patient and encapsulates the data in packets and sends the packets over a network to the central monitoring station. Since the information is encapsulated in packets, the information can be sent over multiple types or combination of network architectures, including a community access television (CATV) network, the public switched telephone network (PSTN), the integrated services digital network (ISDN), the Internet, a local area network (LAN), a wide area network (WAN), over a wireless communications network, or over asynchronous transfer mode (ATM) network. A separate transmission code is not required for each different type of transmission media.

One of the advantages of the Pfeifer invention is that it enables data of various forms to be formatted in a single packet irrespective of the origin or medium of transmission. However, the data transfer system lacks the capability to remotely debug or optimize the performance parameters of the medical interface device or the programmer. Further, Pfeifer does not disclose a method or structure by which the devices at the patient monitoring station may be remotely optimized for patient safety or benefit.

In a related art, Thompson discloses a patient tracking system in U.S. Pat. No. 6,083,248 entitled "World-wide Patient Location and Data Telemetry System For Implantable Medical Devices", issued on Jul. 4, 2000, which is incorporated by reference herein in its entirety. The '248 patent provides additional features for patient tracking in a mobile environment worldwide via the GPS system. However, the notification of recalled parts and upgradeable units advanced by the present invention are not within the purview of the Thompson disclosure because there is no teaching of a web-based environment in which a programmer or an interface medical unit (IMU) is used to transfer IMD data for monitoring and to alert the patient and clinician about safety and function improvements to the IMD units.

Yet in another related art, Ferek-Petric discloses a system for communication with a medical device in a co-pending application, Ser. No. 09/348,506, "System for Remote Communication with a Medical Device," filed Jul. 7, 1999, which is incorporated by reference herein in its entirety. The disclosure relates to a system that enables remote communications with a medical device, such as a programmer. Particularly, the system enables remote communications to inform device experts about programmer status and problems, the experts will then provide guidance and support remotely to service personnel or operators located at the programmer. The system may include a medical device adapted to be implanted into a patient; a server PC (SPC) communicating with the medical device; the server PC having means for receiving data transmitted across a dispersed data communication pathway, such as the Internet; and a client PC having means for receiving data transmitted across a dispersed communications pathway from the SPC. In certain configurations the SPC may have means for transmitting data across a dispersed data communication pathway (Internet) along a first channel and a second channel; and the client PC may have means for receiving data across a dispersed communication pathway from the SPC along a first channel and a second channel.

One of the significant teachings of Ferek-Petric's disclosure, in the context of the present invention, includes the implementation of communication systems, associated with IMDs that are compatible with the Internet. Specifically the disclosure advances the art of remote communications between a medical device, such as a programmer, and experts located at a remote location using the Internet. As indicated hereinabove, the communications scheme is structured to primarily alert remote experts to existing or impending problems with the programming device so that prudent action, such as early maintenance or other remedial steps, may be timely exercised. Further, because of the early warning or advance knowledge of the problem, the remote expert would be well informed to provide remote advice or guidance to service personnel or operators at the programmer.

While Ferek-Petric's invention advances the art in communications systems relating to interacting with a programmer via a communication medium such as the Internet, the system does neither propose nor suggest the notification/recommendation system advanced by the present invention.

In yet another related art Knapp discloses a medical information transponder implant and tracking system in U.S. Pat. No. 5,855,609 issued on Jan. 5, 1999. The disclosure relates to a passive electrical transponder directly transplanted in a patient's underarm area. Medical devices may also carry transponders to identify them for use with the tracking system of the invention. An identification code is accessed with an electromagnetic hand held reader, which is brought into proximity of the transponder. The medical information may itself be directly encoded into the transponder, or a code used which is then keyed to a corresponding data entry in a data bank or computerized database accessible over telecommunication lines. Accordingly, medical information may be reliably and confidentially recorded and accessed confidentially.

While the Knapp disclosure advances the art of medical information collection for both short term and extended time periods for analysis to generate recall notices and to provide generalized health services, it fails far short of the advances brought about by the present invention. Specifically the present invention provides a statistical survival probability projection based upon the implanted base of IMD units to inform patients and their caregivers to allow optimization of IMD safety and function and improve patient benefits of the therapy provided on a real time basis. More specifically the present invention utilizes a programmer or equivalent interface unit that monitors one or more implanted devices on a chronic basis. The interface unit also transfers the information thus collected to a preferably web enabled expert data center for evaluation, analysis and follow-up. In the process, the implanted devices in the patient are checked against a list of measured parameter limits and projections from a remote database. In the event one or more of the devices measured characteristics are found to be out of specification, the clinician and the patient are notified via a preferably web-enabled communication network.

In yet another related art, in U.S. Pat. No. 5,391,193, Thompson discloses a method and apparatus for estimating the remaining capacity of a lithium-iodine battery through the nomographic analysis of two or more measurements of battery impedance. In a preferred embodiment, a pacemaker or other implantable medical device is provided with circuitry for periodically measuring the internal impedance of its battery. Each measurement of impedance is stored along with an indication of when such measurement was made. Nomographic analysis, based upon the rated capacity of the battery and the expected internal impedance at various stages of depletion, allows for two or more time-stamped impedance measurements to serve as the basis for an extrapolation to estimate the remaining service life of the implantable medical device. Nomographic analysis may be performed by circuitry contained in the implanted device itself; in the alternative, periodic impedance measurements may be communicated to external processing circuitry via a telemetry channel. This system does not use a remote integrated database of statistical survival probability projections to aid in the management of patient safety and IMD longevity actions.

In yet another related art, in U.S. Pat. No. 4,979,507, Heinz discloses a system that has as an objective the universal matching of individual patient-pacemaker-implant electrode interface conditions to follow dynamic changes occurring in use, from pacemaker to pacemaker and from patient to patient to control the pacing pulse energy in operation most efficiently to prolong battery life. Information from the implanted stimulation electrode is analyzed to discriminate the energy level of pulses effective and ineffective to stimulate a heartbeat for at least two different stimulation pulse characteristics. This analyzed information is automatically processed in logic circuits to conform to the requirements of particular pacemaker adjustments to develop an optimized energy pacing pulse with adequate safety margin. Programming and logic equipment can be in the pacemaker, but additional energy saving with those calculations takes place when it is external to the pacemaker and bi-directional communication of information takes place with the pacemaker. Periodic automatic programming can take place in implanted pacemaker installations for continuous long term monitoring and control to obtain the optimum battery life and adequate safety standards. This system does not use a remote integrated database of statistical survival probability projections to aid in the management of patient safety and IMD longevity actions.

In yet another related art, in U.S. Pat. No. 5,620,474, Koopman describes a programmable pacing system and method, the system having the capability for providing an indication of recommended replacement time (RRT) as well as a prior warning of six months to RRT. RRT is determined by storing a value in the pacemaker corresponding to battery impedance at RRT, continuously periodically measuring battery impedance, and comparing the measured value with the stored RRT value. Whenever the pacemaker is reprogrammed to different operating conditions which affect RRT, or there is a significant change in load lead resistance, a new value of RRT impedance is calculated based upon a selected formula corresponding to the reprogrammed set of operating conditions, and stored in the pacemaker. At the same time, an aging value of impedance is re-calculated to provide a six-month warning before RRT, and likewise stored in the pacemaker. This system does not use a remote integrated database of statistical survival probability projections to aid in the management of patient safety and IMD longevity actions.

In yet another related art, in U.S. Pat. No. 5,309,919, Snell describes a method and system for monitoring the behavior of an implanted pacemaker counts (records) the number of times that a given internal event or state change of the pacemaker occurs, and also determines the rate at which each event or state change thus counted occurs. The event counts and their associated rate are stored (recorded) in appropriate memory circuits housed within the pacemaker device. At an appropriate time, the stored event count and rate data are downloaded to an external programming device. The external programming device processes the event count and rate data, and displays a distribution of the event count data as a function of its rate of occurrence, as well as other statistical information derived therefrom. The displayed information, and its associated statistical information, allows a baseline recording to be made that establishes the implanted pacemaker's behavior for a given patient under known conditions. Such baseline recording of event counts in combination with the associated rate of occurrence of such event counts provides significant insight into the past behavior of the pacemaker as implanted in a particular patient. The past behavior of the pacemaker, in turn, may then be used to predict with a high degree of accuracy the future behavior of the pacemaker. This system does not use a remote integrated database of statistical survival probability projections to aid in the management of patient safety and IMD longevity actions.

Accordingly, it would be desirable to provide a system in which one or more implanted devices could uplink to a remote expert data center via an interface medical unit such as a programmer to access a patient and device information database to identify devices or components out of specification and notify the clinician and/or patient as apparent. Yet another desirable advantage would be to provide a system to implement the use of remote expert systems to optimally manage IMDs on a real-time basis. A further desirable advantage would be to provide a communications scheme that is compatible with various communications media, to promote a fast uplink of a programmer to remote expert systems and specialized data resources to chronically monitor IMDs and provide an uninterrupted management of patient therapy and clinical care. Yet another desirable advantage would be to provide a high speed communications scheme to enable the transmission of high fidelity sound, video and data to advance and implement efficient remote data management of a clinical/therapy system via a programmer or an interface medical unit thereby enhancing patient clinical care. Yet a further desirable advantage would be to remotely import a software-based patient and device information for use by local clinicians/operators/technicians using programmers for IMDs distributed throughout the world. Preferably, a remote web-based expert data center would direct, update, command and control a software-based information system worldwide to keep an interconnected scheme in which, among other services, information about improving patient safety and benefit from IMDs are kept for alerting patients or care givers, as needed. As discussed herein below, the present invention provides these and other desirable advantages.

SUMMARY OF THE INVENTION

The present invention generally relates to a communications scheme in which a remote web-based expert data center interacts with a patient having one or more implantable medical devices (IMDs) via an associated external medical device, preferably a programmer or an interface medical unit (IMU), located in close proximity to the IMDs. Some of the most significant elements of the invention include the use of various communications media between the remote web-based expert data center and the programmer to remotely exchange clinically significant information and ultimately effect real-time parametric and operational changes as needed.

In the context of the present invention, one of the many aspects of the invention includes a real-time access of a programmer or an IMD to a remote web-based expert data center, via a communication network, which includes the Internet. The operative structure of the invention includes the remote web-based expert data center, in which an expert system is maintained, having a bi-directional real-time data, sound and video communications with the programmer via a broad range of communication link systems. The programmer is in turn in telemetric communications with the IMDs such that the IMDs may uplink to the programmer or the programmer may down link to the IMDs, as needed.

In a further context of the invention, a programmer is remotely monitored, assessed and upgraded as needed by importing expert systems from a remote expert data center via a wireless or equivalent communications system. The operational and functional software of the embedded systems in the programmer may be remotely adjusted, upgraded or changed to ultimately be implemented in the IMDs as needed by down linking from the programmer to the IMDs.

Yet another context of the invention includes a communications scheme that provides a highly integrated and efficient method and structure of clinical information management in which various networks such as Community access Television, Local area Network (LAN), a wide area network (WAN) Integrated Services Digital Network (ISDN), the Public Switched telephone Network (PSTN), the Internet, a wireless network, an asynchronous transfer mode (ATM) network, a laser wave network, satellite, mobile and other similar networks are implemented to transfer voice, data and video between the remote data center and a programmer. In the preferred embodiment, wireless communications systems, a modem and laser wave systems are illustrated as examples only and should be viewed without limiting the invention to these types of communications alone. Further, in the interest of simplicity, the applicants refer to the various communications system, in relevant parts, as a communication system. However, it should be noted that the communication systems, in the context of this invention, are interchangeable and may relate to various schemes of cable, fiber optics, microwave, radio, laser and similar communications or any practical combinations thereof.

Yet one of the other distinguishing features of the invention includes the use a highly flexible and adaptable communications scheme to promote continuous and real-time communications between a remote expert data center and a programmer associated with a plurality of IMDs. The IMDs are structured to share information intracorporeally and may interact with the programmer or IMU, as a unit. Specifically, the IMDs either jointly or severally can be interrogated to implement or extract clinical information as required. In other words, all of the IMDs may be accessed via one IMD or, in the alternate, each one of the IMDs may be accessed individually. The information collected in this manner may be transferred to the programmer by up linking the IMDs as needed.

Further, the present invention provides significant distinctions over the prior art by enabling remote troubleshooting, maintenance and recommendations for patient safety and program enhancements to the IMDs. The communications scheme enables remote debugging, projections and analysis on the programmer. In the event a component defect or end of life projection is nearing, the system is able to check whether a 'remote-fix' and/or programming change is possible. If not, the system broadcasts an alert to clinician thus attending to the problem on a real-time basis. In the execution of this function the communications scheme of the present invention performs, inter alia, a review of usage logs, error logs, power and battery status, database integrity and the projected mean time to failure status of all the significant and relevant components. Further, patient history, performance parameter integrity from the remote expert data center and the IMDs' diagnostic data are mined from the programmer's database and analyzed by an analyzer resident in the programmer.

The invention provides significant compatibility and scalability to other web-based applications such as telemedicine and emerging web-based technologies such as tele-immersion. For example, the system may be adapted to webtop applications in which a IMU may be used to uplink the patient to a remote data center for non-critical information exchange between the IMDs and the remote expert data center. In these and other web-based similar applications the data collected, in the manner and substance of the present invention, may be used as a preliminary screening to identify the need for further intervention using the advanced web technologies.

More significantly, the invention provides a system and method to remotely alert the patients/clinician if there are out of specification, or about to be out of specification, devices or components of an implantable medical device. Further, the invention enables the patient/clinician to be aware of IMDs requiring increased follow-up frequency and programming changes. Furthermore, the invention enables the patient/clinician to access web sites tailored to provide pertinent information regarding the patient's IMDs and general clinical profile.

BRIEF DESCRIPTION OF THE DRAWINGS

The present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DESCRIPTION OF THE PREFERRED EMBODIMENTS

Figure 1:
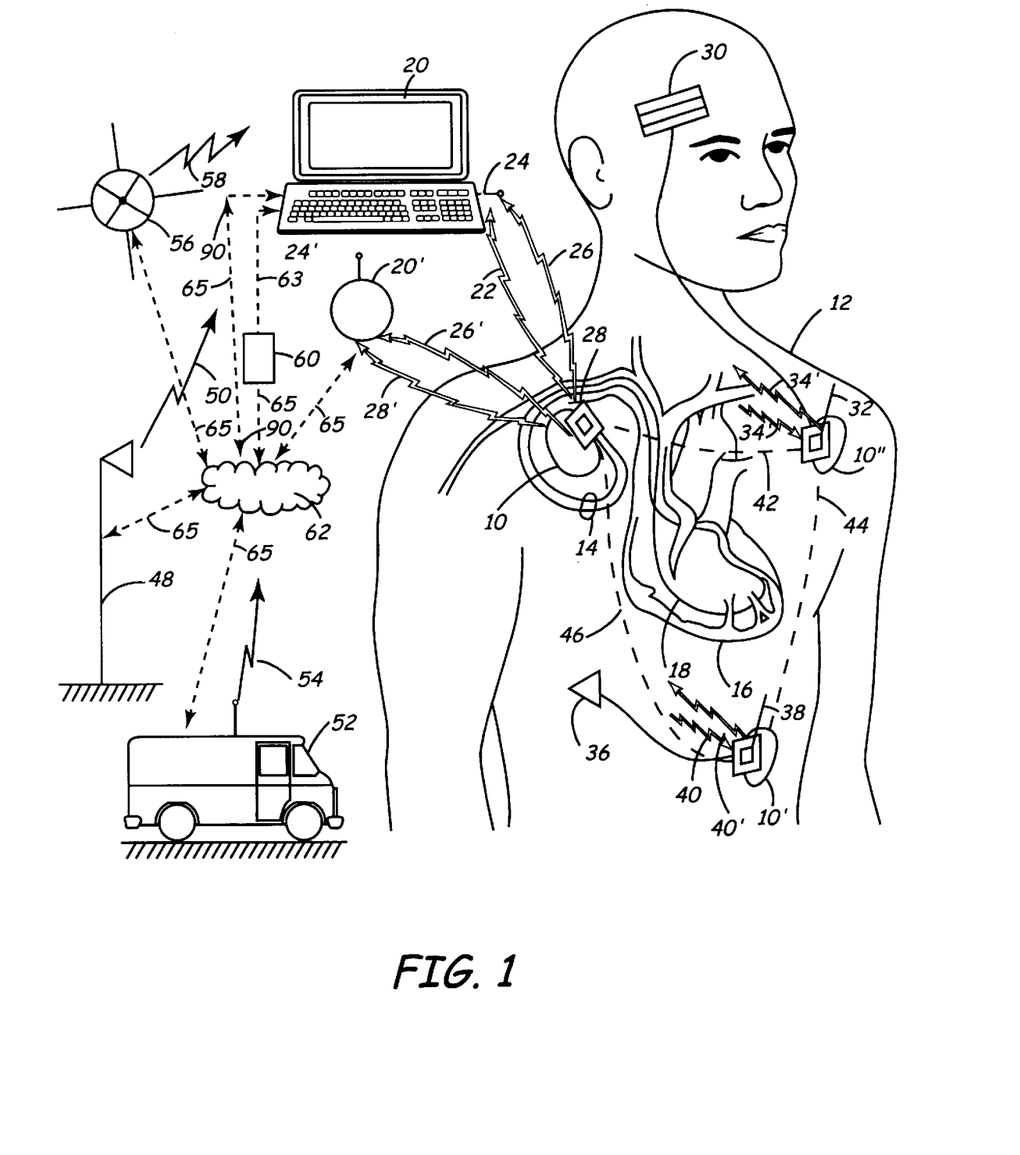
FIG. 1 is a simplified schematic diagram of major uplink and downlink telemetry communications between a remote clinical station, a programmer and a plurality of implantable medical devices (IMDs)

FIG. 1 is a simplified schematic of the major components of the present invention. Specifically, a bi-directional wireless communications system between programmer 20, interface medical unit (IMU) 20' and a number of implantable medical devices (IMDS) represented by IMD 10, IMD 10' and IMD 10" is shown. The IMDs are implanted in patient 12 beneath the skin or muscle. The IMDs are electrically coupled to electrodes 18, 30, and 36 respectively in a manner known in the art. IMD 10 contains a microprocessor for timing, sensing and pacing functions consistent with preset programmed functions. Similarly, IMDs 10' and 10" are microprocessor-based to provide timing and sensing functions to execute the clinical functions for which they are employed. For example, IMD 10' could provide neural stimulation to the brain via electrode 30 and IMD 10" may function as a drug delivery system that is controlled by electrode 36. The various functions of the IMDs are coordinated using wireless telemetry. Wireless links 42, 44 and 46 jointly and severally couple IMDs 10, 10' and 10" such that programmer 20 may transmit commands or data to any or all the of IMDs via one of telemetry antennas 28, 32 and 38. This structure provides a highly flexible and economical wireless communications system between the IMDs. Further, the structure provides a redundant communications system, which enables access to any one of a multiplicity of IMDs in the event of a malfunction of one or two of antennas 28, 32 and 38.

Programming commands or data are transmitted from programmer 20 to IMDs 10, 10' and 10" via external RF telemetry antenna 24. Telemetry antenna 24 may be an RF head or equivalent. Antenna 24 may be located on programmer 20 externally on the case or housing. Telemetry antenna 24 is generally telescoping and may be adjustable on the case of programmer 20. Both programmer 20 and IMU 20' may be placed a few feet away from patient 12 and would still be within range to wirelessly communicate with telemetry antennas 28, 32 and 38.

The uplink to remote web-based expert data center 62, hereinafter referred to as, interchangeably, "data center 62", "expert data center 62" or "web-based data center 62" without limitations, is accomplished through programmer 20 or IMU 20'. Accordingly programmer 20 and IMU 20' function as an interface between IMDs 10, 10' and 10" and data center 62. One of the many distinguishing elements of the present invention includes the use of various scalable, reliable and high-speed wireless communication systems to bi-directionally transmit high fidelity digital/analog data between programmer 20 and data center 62.

There are a variety of wireless mediums through which data communications could be established between programmer 20 or IMU 20' and data center 62. The communications link between Programmer 20 or IMU 20' and data center 62 could be modem 60, which is connected to programmer 20 on one side at line 63 and data center 62 at line 64 on the other side. In this case, data is transferred from data center 62 to programmer 20 via modem 60. Alternate data transmission systems include, without limitations, stationary microwave and/or RF antennas 48 being wirelessly connected to programmer 20 via tunable frequency wave delineated by line 50. Antenna 48 is in communications with data center 62 via wireless link 65. Similarly, IMU 20', mobile vehicle 52 and satellite 56 are in communications with data center 62 via wireless link 65. Further, mobile system 52 and satellite 56 are in wireless communications with programmer 20 or IMU 20' via tunable frequency waves 54 and 58, respectively.

In the preferred embodiment a Telnet system is used to wirelessly access data center 62. Telnet emulates a client/server model and requires that the client run a dedicated software to access data center 62. The Telnet scheme envisioned for use with the present invention includes various operating systems including UNIX, Macintosh, and all versions of Windows.

Functionally, an operator at programmer 20, an operator at data center 62 or a clinician/physician at center 66 would initiate remote contact. Programmer 20 is down linkable to IMDs via link antennas 28, 32 and 38 to enable data reception and transmission. For example, an operator or a clinician at data center 62 may downlink to programmer 20 to perform a routine or a scheduled evaluation of programmer 20. In this case the wireless communication is made via wireless link 65. If a downlink is required from programmer 20 to IMD 10 for example, the downlink is effected using telemetry antenna 22. In the alternate, if an uplink is initiated from patient 12 to programmer 20 the uplink is executed via wireless link 26. As discussed herein below, each antenna from the IMDs can be used to uplink all or one of the IMDs to programmer 20. For example, IMD 10" which relates to neural implant 30 can be implemented to up-link, via wireless antenna 34 or wireless antenna 34', any one, two or more IMDs to programmer 20. Preferably Bluetooth chips, adopted to function within the body to outside the body and also adopted to provide low current drain, are embedded in order to provide wireless and seamless connections 42, 44 and 46 between IMDs 10, 10' and 10". The communication scheme is designed to be broadband compatible and capable of simultaneously supporting multiple information sets and architecture, transmitting at relatively high speed, to provide data, sound and video services on demand.

Figure 2:
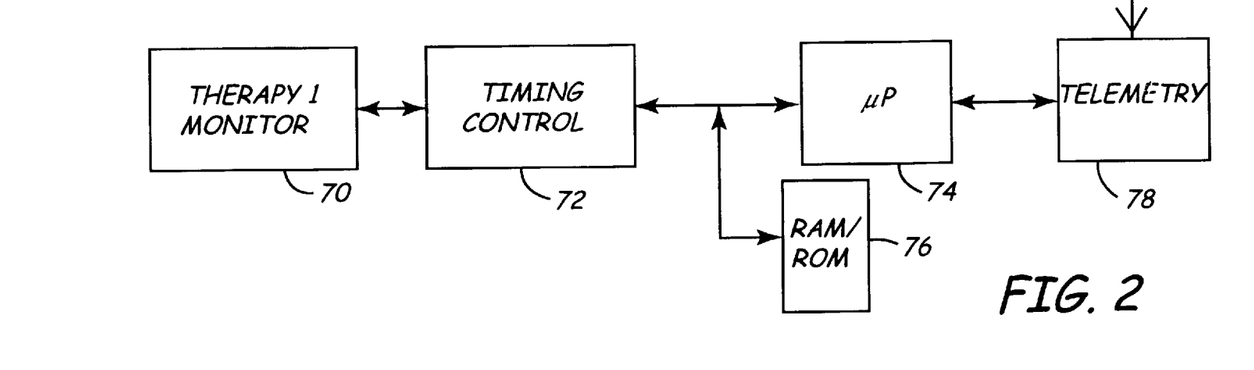
FIG. 2 is a block diagram representing the major components of an IMD.

FIG. 2 illustrates typical components of an IMD, such as those contemplated by the present invention. Specifically, major operative structures common to all IMDs 10, 10' and 10" are represented in a generic format. In the interest of brevity, IMD 10 relative to FIG. 2 refers to all the other IMDs. Accordingly, IMD 10 is implanted in patient 12 beneath the patient's skin or muscle and is electrically coupled to heart 16 of patient 12 through pace/sense electrodes and lead conductor(s) of at least one cardiac pacing lead 18 in a manner known in the art. IMD 10 contains timing control 72 including operating system that may employ microprocessor 74 or a digital state machine for timing, sensing and pacing functions in accordance with a programmed operating mode. IMD 10 also contains sense amplifiers for detecting cardiac signals, patient activity sensors or other physiologic sensors for sensing the need for cardiac output, and pulse generating output circuits for delivering pacing pulses to at least one heart chamber of heart 16 under control of the operating system in a manner well known in the prior art. The operating system includes memory registers or RAM/ROM 76 for storing a variety of programmed-in operating mode and parameter values that are used by the operating system. The memory registers or RAM/ROM 76 may also be used for storing data compiled from sensed cardiac activity and/or relating to device operating history or sensed physiologic parameters for telemetry out on receipt of a retrieval or interrogation instruction. Stored data relating to device operating history constitutes IMD "performance logs." All of these functions and operations are well known in the art, and many are generally employed to store operating commands and data for controlling device operation and for later retrieval to diagnose device function or patient condition.

Programming commands or data are transmitted between IMD 10 RF telemetry antenna 28, for example, and an external RF telemetry antenna 24 associated with programmer 20. In this case, it is not necessary that the external RF telemetry antenna 24 be contained in a programmer RF head so that it can be located close to the patient's skin overlying IMD 10. Instead, the external RF telemetry antenna 24 can be located on the case of programmer 20. It should be noted that programmer 20 can be located some distance away from patient 12 and is locally placed proximate to the IMDs such that the communication between IMDs 10, 10' and 10" and programmer 20 is telemetric. For example, programmer 20 and external RF telemetry antenna 24 may be on a stand a few meters or so away from patient 12. Moreover, patient 12 may be active and could be exercising on a treadmill or the like during an uplink telemetry interrogation of real-time ECG or other physiologic parameters. Programmer 20 may also be designed to universally program existing IMDs that employ RF telemetry antennas of the prior art and therefore also have a conventional programmer RF head and associated software for selective use therewith.

In an uplink communication between IMD 10 and programmer 20, for example, telemetry transmission 22 is activated to operate as a transmitter and external RF telemetry antenna 24 operates as a telemetry receiver. In this manner data and information may be transmitted from IMD 10 to programmer 20. In the alternate, IMD 10 RF telemetry antenna 26 operates as a telemetry receiver antenna to downlink data and information from programmer 20. Both RF telemetry antennas 22 and 26 are coupled to a transceiver comprising a transmitter and a receiver.

Figure 3A:
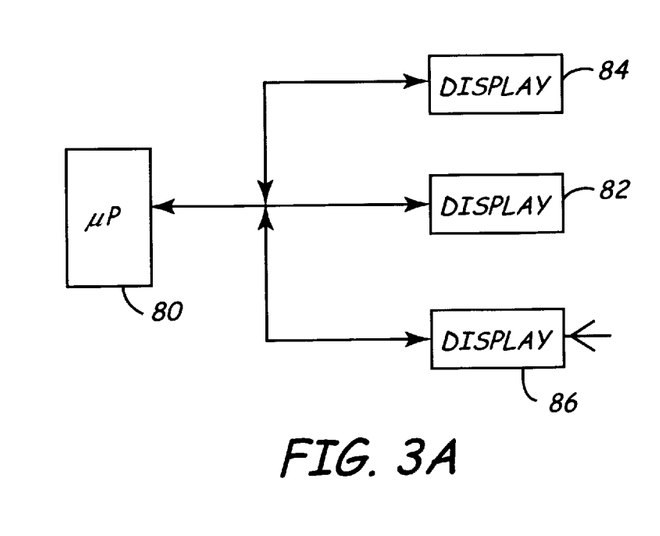
FIG. 3A is a block diagram presenting the major components of a programmer or IMU.

FIG. 3A is a simplified circuit block diagram of major functional components of programmer 20. The external RF telemetry antenna 24 on programmer 20 is coupled to a telemetry transceiver 86 and antenna driver circuit board including a telemetry transmitter and telemetry receiver 34. The telemetry transmitter and telemetry receiver are coupled to control circuitry and registers operated under the control of microcomputer 80. Similarly, within IMD 10, for example, the RF telemetry antenna 26 is coupled to a telemetry transceiver comprising a telemetry transmitter and telemetry receiver. The telemetry transmitter and telemetry receiver in IMD 10 are coupled to control circuitry and registers operated under the control of microcomputer 74.

Further referring to FIG. 3A, programmer 20 is a personal computer type, microprocessor-based device incorporating a central processing unit, which may be, for example, an Intel Pentium microprocessor or the like. A system bus interconnects CPU 80 with a hard disk drive, storing operational programs and data, and with a graphics circuit and an interface controller module. A floppy disk drive or a CD ROM drive is also coupled to the bus and is accessible via a disk insertion slot within the housing of programmer 20. Programmer 20 further comprises an interface module, which includes a digital circuit, a non-isolated analog circuit, and an isolated analog circuit. The digital circuit enables the interface module to communicate with interface controller module. Operation of the programmer in accordance with the present invention is controlled by microprocessor 80.

In order for the physician or other caregiver or operator to communicate with the programmer 20, a keyboard or input 82 coupled to CPU 80 is optionally provided. However the primary communications mode may be through graphics display screen of the well-known "touch sensitive" type controlled by a graphics circuit. A user of programmer 20 may interact therewith through the use of a stylus, also coupled to a graphics circuit, which is used to point to various locations on screen or display 84 which display menu choices for selection by the user or an alphanumeric keyboard for entering text or numbers and other symbols. Various touch-screen assemblies are known and commercially available. Display 84 and or the keyboard comprise means for entering command signals from the operator to initiate transmissions of downlink or uplink telemetry and to initiate and control telemetry sessions once a telemetry link with data center 62 or an implanted device has been established. Display screen 84 is also used to display patient related data and menu choices and data entry fields used in entering the data in accordance with the present invention as described below. Display screen 84 also displays a variety of screens of telemetered out data or real-time data. Display screen 84 may also display uplinked event signals as they are received and thereby serve as a means for enabling the operator to timely review link-history and status.

Programmer 20 further comprises an interface module, which includes digital circuit, non-isolated analog circuit, and isolated analog circuit. The digital circuit enables the interface module to communicate with the interface controller module. As indicated hereinabove, the operation of programmer 20, in accordance with the present invention, is controlled by microprocessor 80. Programmer 20 is preferably of the type that is disclosed in U.S. Pat. No. 5,345,362 to Winkler, which is incorporated by reference herein in its entirety.

Display screen 84 may also display up-linked event signals when received and thereby serve as a means for enabling the operator of programmer 20 to correlate the receipt of uplink telemetry from an implanted device with the application of a response-provoking action to the patient's body as needed. Programmer 20 is also provided with a strip chart printer or the like coupled to interface controller module so that a hard copy of a patient's ECG, EGM, marker channel of graphics displayed on the display screen can be generated.

As will be appreciated by those of ordinary skill in the art, it is often desirable to provide a means for programmer 20 to adapt its mode of operation depending upon the type or generation of implanted medical device to be programmed and to be compliant with the wireless communications system through which data and information is transmitted between programmer 20 and data center 62.

Figure 3B:
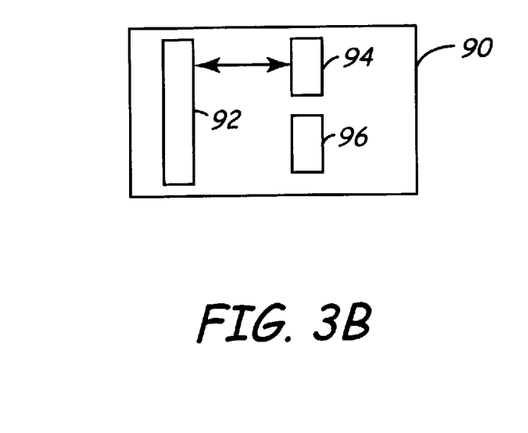
FIG. 3B is a block diagram representing a laser transceiver for high-speed transmission of voice, video and other data.

FIG. 3B is an illustration of the major components of Wave unit 90 utilizing laser technologies such as for example the WaveStar Optic Air Unit, manufactured by Lucent Technologies or equivalent. This embodiment may be implemented for large data transfer at high speed in applications involving several programmers. The unit includes laser 92, transceiver 94 and amplifier 96. A first wave unit 90 is installed at data center 62 and a second unit 90' is located proximate to programmer 20 or IMU 20'. Data transmission between remote data center 62 and programmer unit 20 is executed via wave units 90. Typically, the first wave unit 90 accepts data and splits it into unique wavelength for transmission. The second wave unit 90' recomposes the data back to its original form.

Figure 4:
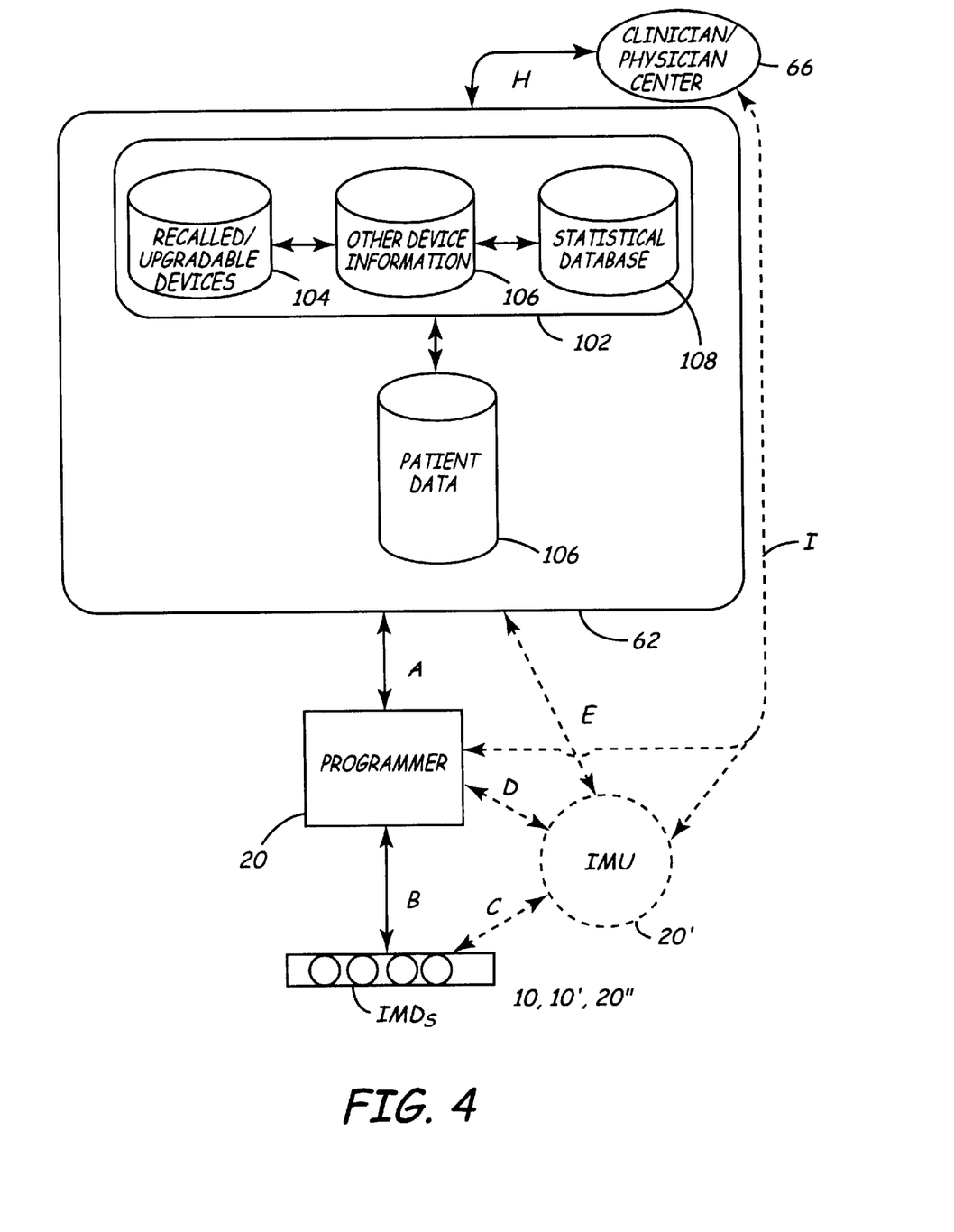
FIG. 4 is a block diagram illustrating the organizational structure of the communication system between the various functional units and the remote expert data center in accordance with the present invention.

FIG. 4 is a simplified block diagram illustrating the principal systems of the invention. The Remote expert system or data center 62 includes patient data 100. Further, data center 62 includes device database 102. Database 102 further includes recalled/up-gradable devices database 104, other device information 106 and statistical projected survival database for all of Medtronic's™ products 108. Under normal operations, an uplink is initiated by the clinician/physician at center 66. In the alternate, the clinician/physician center may be one and the same as remote center 62. Remote center 62 is preferably web-enabled and includes high speed computer resources and software (not shown) adapted for data storage, analysis and management to provide rapid data exchange between programmer 20 or IMU 20' and clinician/physician center 66. The various remote centers including data center 62 and clinician center 66 are connected via wireless or equivalent communication channels to provide real-time data, sound and video exchange between programmer 20, IMU 20', IMDs 10, 10' and 10". In the context of the present invention, when either programmer 20 or IMU 20' is remotely linked via link A or E, respectively, to data center 62, access is made to patient database 100. Information on IMDs 10, 10' and 10" is transmitted through up-link connection B or C to either programmer 20 or IMU 20', respectively. The information is compared with patient database 100 at remote data center 62. Patient database then searches to match the information from IMDs 10, 10' and 10" with recalled/up-gradable devices database 104 which may be specific to the products made by several manufacturers. Further, the information is also compared with the statistical information database 108 such as, for example, device projected longevity estimates, lead impedance measurements, measured pacing and sensing thresholds, and long-term clinical data. Thus, in addition to providing the various clinical and therapeutic management functions based on the communications between the patient station, remote data center 62 and clinician/physician center 66, the invention enables the implementation of a proactive alert system to inform patients of recalled, obsolete or up-gradable units needing replacement, and optimization of therapy, safety and benefit for the patient.

Figure 5:
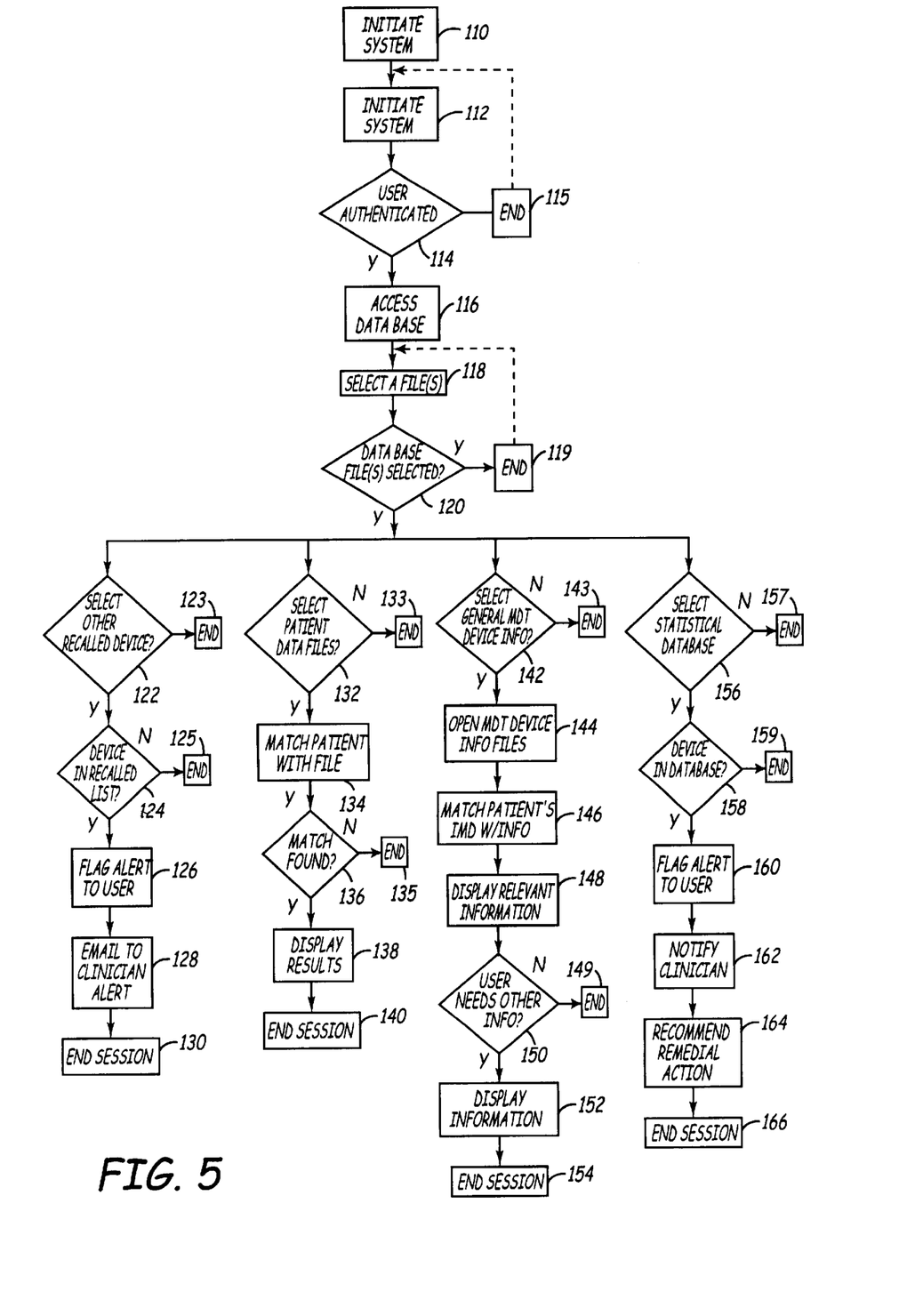
FIG. 5 is a logic flow chart representing high-level steps of the software program in accordance with the present invention.

Referring to FIG. 5, a high-level software logic operating the alert system of the present invention is disclosed. Specifically, the system is initiated under logic step 110. The logic proceeds to step 112 where access to remote data center is allowed. Thereafter, the user is authenticated under logic step 114. If the user is not certified, the logic proceeds to end at step 115. If the user is granted access, the logic advances to step 116 where the database in remote center 62 is accessed. Subsequently, the user is served a set of menus displaying a selection of a file or files for access. The user then selects a file or files under logic step 118. The logic proceeds to decision step 120 to check if any file(s) is selected. If no file is selected, the sequence is ended under step 119 and/or the program enters a subroutine where the user is prompted to select a file(s) before further access to subsequent logic steps is allowed. In the event a database for a certain file(s) is selected the program proceeds to decision step 122. If the selection is not to access database 104 the logic proceeds to step 123 where the access to the file is ended. If the choice is to access database 104, the logic proceeds to decision block 124 where the user's IMDs or the information relating to the IMDs is located in database 104. If the device in question is not found to be in the list of recalled or up-gradable devices, the logic proceeds to step 125 and the program is terminated. In the alternate, if the device is found to be in the list of recalled or up-gradable devices, relating to products made by manufacturers other than Medtronic™, an alert flag is set under logic step 126. Subsequently, an E-mail alert or equivalent is sent to the clinician or the operator responsible for managing the patient's data under step 128 and the session ends at step 130.

If the user elects to access patient data files, the program logic proceeds to decision step 132. The system confirms if the user wants to access the patient data files 100. In the event the user does not want to proceed with this choice, the program is terminated at step 133. However, if the user wants to review or access patient data 100, the program logic advances to logic step 134 and searches the file automatically to match it with the IMDs and related data specific to the user or the patient. Subsequently, the logic proceeds to decision block 136 to check if a match is found. If no match is located the program ends at step 135. If a match is found, however, the program advances to step 138 to display the results of the match. The results of the match may include specific patient information including the IMDs and pertinent clinical and therapy information.

Yet another alternate choice could be for the user to access other device information or general Medtronic™ device information file 106 under decision block 142. The program logic confirms if this is the choice or otherwise it will be terminated under step 143. After the selection is confirmed, however, the program logic proceeds to step 144 where the Medtronic™ device information file 106 is opened. Thereafter, the patient's IMDs are compared with resident data and information under logic step 146. Subsequently, relevant information is displayed, as required by the user, under logic step 148. The program logic proceeds to decision block 149 where the need for further information is checked under logic step 150. If the user indicates not to proceed any further, the program is terminated at step 149. If the user elects to get further information, the system displays the additional information under logic step 152 and the session ends at step 154.

Yet another selection could be the user may elect to review or access database 108 relating to the optimization of therapy, estimate remaining longevity, suggest follow-up frequency changes, and verify device functionality. If this is not the user's selection the program is terminated at logic step 157. If however, the user requests to access database 108, the program logic proceeds to decision step 158 to check if the user's or patient's IMDs match the list of Medtronic™ products with available function tests and projections. If there is no match the program is terminated at logic step 159. In the alternate if a match is found, a flag is displayed to alert the user under logic step 160. The clinician is then notified under logic step 162 to make sure that a clinical follow-up is undertaken. Further, the program posts a recommended course of action under logic step 164. The program is then terminated under logic step 166.

In this manner, a patient is enabled to access patient data 100, recalled device/upgrade file 104, general device/ other device information file 106 and Medtronic™ statistical database 108 files remotely via programmer 20 or IMU 20'. Specifically, the invention enables the patient or manager of IMDs 10, 10' and 10" to access remote data center 62 to use various resources and databases. Further, the system enables clinicians and physicians at remote station 66 to access databases relating to patient data and product information. Additionally, remote clinician or physician station 66 is in data communications with IMDs 10, 10', 10" and programmer 20 or IMU 20' via link I. Although the primary aspect of the invention relates to accessing patient and/or device related databases, another aspect of the invention provides transfer of device and patient information to the remote database. Specifically, the scheme disclosed in the present invention may enable user/operator to transfer data to remote data center via programmer 20 or IMU 20', allowing each additional patient implanted with a device and subsequent follow-up information to augment the remote database statistical probability data.

As discussed hereinabove, data center 62 is preferably in wireless communications with programmer 20 or IMU 20'. The medium of communications between programmer 20 and data center 62 may be selected from one or a combination of several cable and wireless systems discussed hereinabove. Further, programmer 20 is in wireless communications with a number of IMDs, such as shown in FIG. 1. Although three IMDs are shown for illustrative purposes, it should be noted that several IMDs may be implemented and the practice of the present invention does not limit the number of implants per se.

Referring to programmer 20 in more detail, when a physician or an operator needs to interact with programmer 20, a keyboard coupled to Processor 80 is optionally employed. However the primary communication mode may be through graphics display screen of the well-known "touch sensitive" type controlled by graphics circuit. A user of programmer 20 may interact therewith through the use of a stylus, also coupled to a graphics circuit, which is used to point to various locations on a screen/display to display menu choices for selection by the user or an alphanumeric keyboard for entering text or numbers and other symbols as shown in the above-incorporated '362 patent. Various touch-screen assemblies are known and commercially available. The display and or the keyboard of programmer 20, preferably include means for entering command signals from the operator to initiate transmissions of downlink telemetry from IMDs and to initiate and control telemetry sessions once a telemetry link with one or more IMDs has been established. The graphics display /screen is also used to display patient related data and menu choices and data entry fields used in entering the data in accordance with the present invention as described below. Graphics display/ screen also displays a variety of screens of telemetered out data or real-time data. Programmer 20 is also provided with a strip chart printer or the like coupled to an interface controller module so that a hard copy of a patient's ECG, EGM, marker channel or similar graphics display can be generated. Further, Programmer 20's history relating to instrumentation and software status may be printed from the printer. Similarly, once an uplink is established between programmer 20 and any one of IMDs 10, 10' and 10", various patient history data and IMD performance data may be printed out. The IMDs contemplated by the present invention include a cardiac pacemaker, a defibrillator, a pacer-defibrillator, implantable monitor, cardiac assist device, and similar implantable devices for cardiac rhythm and therapy. Further the IMD units contemplated by the present invention include electrical stimulators such as, but not limited to, a drug delivery system, a neural stimulator, a neural implant, a nerve or muscle stimulator or any other implant designed to provide physiologic assistance or clinical therapy.

The communications link/connections such as links A, B, C, D, E, H and I may be one of a variety of links or interfaces, such as a local area network (LAN), an internet connection, a telephone line connection, a satellite connection, a global positioning system (GPS) connection, a cellular connection, a cable connection, a laser wave generator system, any combination thereof, or equivalent data communications links.

As stated hereinabove, the bi-directional wireless communications 136 acts as a direct conduit for information exchange between remote data center 62 and programmer 20. Further, bi-directional wireless communications 136 provides an indirect link between remote data center and IMDs 10, 10' and 10" via programmer 20. In the context of this disclosure the word "data" when used in conjunction with bi-directional wireless communications also refers to sound, video and information transfer between the various centers.

Figure 6:
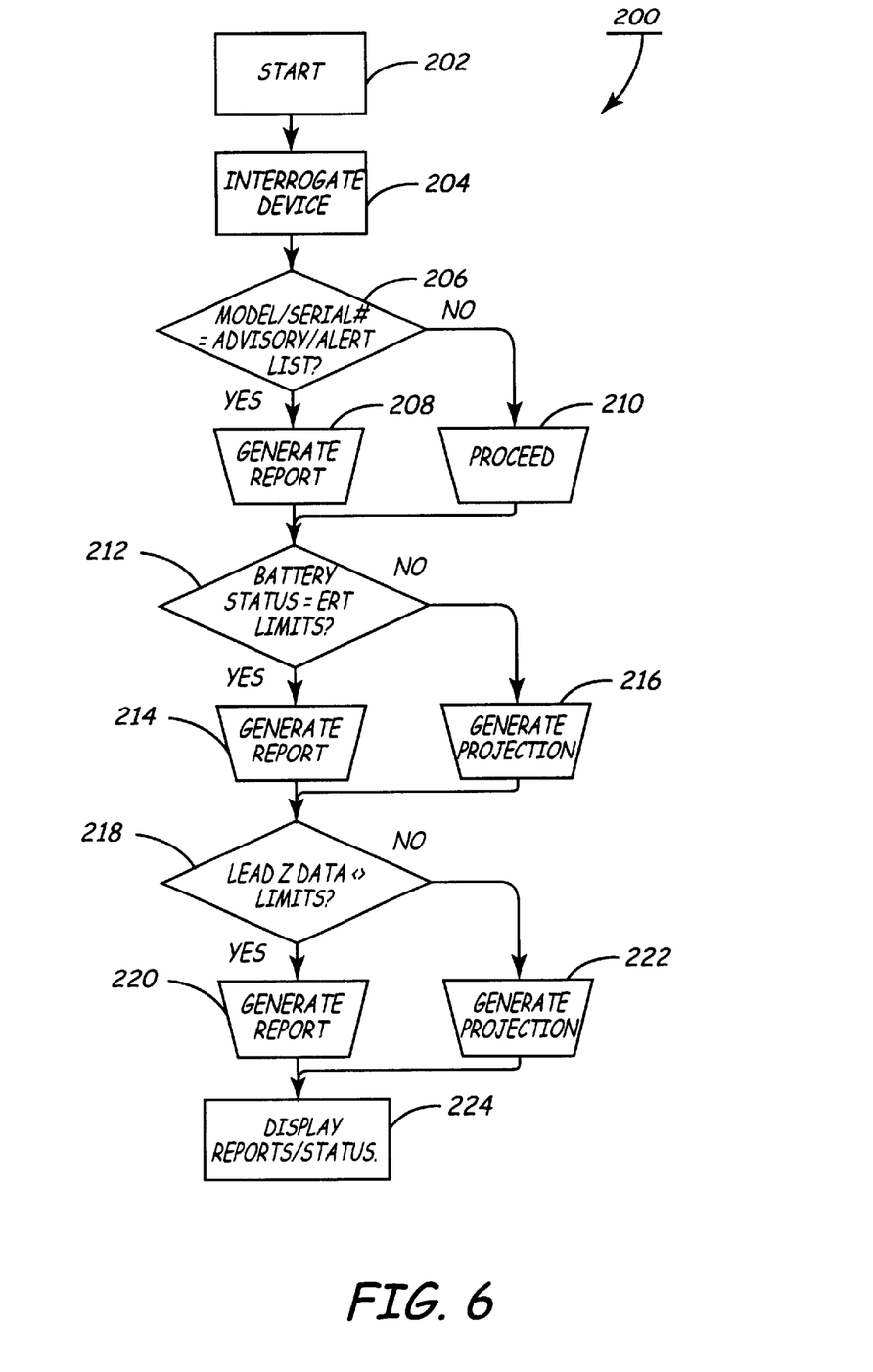
FIG. 6 is a logic flow chart representing the detailed steps of the software program in accordance with the present invention.

FIG. 6 shows a flow diagram 200 of a method of practicing the invention described herein. The method is initiated at step 202 whereby programmer 20 at step 204 interrogates the IMD(S) 10, 10' and 10". The model number and serial number of the IMD is compared to an advisory or recall list at step 206. If the device being interrogated is not on the list, the flow diagram proceeds, via step 210, to step 212. If the IMD is found to be on a list for notification, a report is generated at step 208.

At step 212, the uplinked battery status, battery voltage and/or battery impedance is compared to limits for the particular IMD. Measurements may be made by any of several methods, one as described in U.S. Pat. No. 5,137,020 to Wayne, et, al. Other impedance measurement circuits are also known in the art and believed to be suitable for the purposes of the present invention; see, for example, U.S. Pat. No. 4,606,350 to Frost. Both patents are herein incorporated by reference in their entireties. At step 212, if the battery status is at elective replacement time (e.g., ERT), a report is generated at step 214.

If the battery status is not yet at, or beyond ERT, at step 212, a remaining IMD longevity is projected based upon the survivability probability data as provided by the periodically published Medtronic Product Performance Report (a summary report/projection of the implanted database of all implanted devices of similar model and parameter settings is projected in a statistical survival probability model), the stored diagnostic data from the IMD (e.g., average pacing rate, maximum pacing rate achieved, percent pacing, programmable output pulse settings, frequency and lengths of mode switches, etc.), and the present measured battery voltage or impedance. Diagnostic data stored and subsequently retrieved from the IMD may be as substantially described in U.S. Pat. No. 5,330,513 to Nichols, et. al., incorporated herein by reference in its entirety. At step 218, the measured lead impedance from IMD 10 is compared to limits to verify lead viability, expected longevity, and function per recommendations in the Product Performance Report. As an example, if the lead impedance is less than 250 ohms and/or has changed 30% from the value measured at implant, when measured at step 218, a recommended course of action and report is generated at step 220. This action may include prophylactic replacement of the lead, decreased follow-up intervals, or parameter changes to the IMD (e.g., increased pacing amplitude/pulse width, sensitivity threshold adjustments, mode changes, etc.). If the lead impedance measurements are within normal range, a longevity projection is performed at step 222 based upon the actual impedance measurement and historical data from the implanted database of similar model and parameter settings.

The reports and recommendations generated at steps 208, 214, and 220 may be displayed on the programmer 20 screen and/or printed for insertion into a hardcopy patient file at step 224. These recommendations may be provided to the physician at step 224 to maximize longevity, improve patient benefit and/or increase reliability of device function by adjustment of programmable parameter settings or change courses of medical treatment (e.g., initial choice of device, prophylactic replacement, change of follow-up frequency, etc.).

Figure 7:
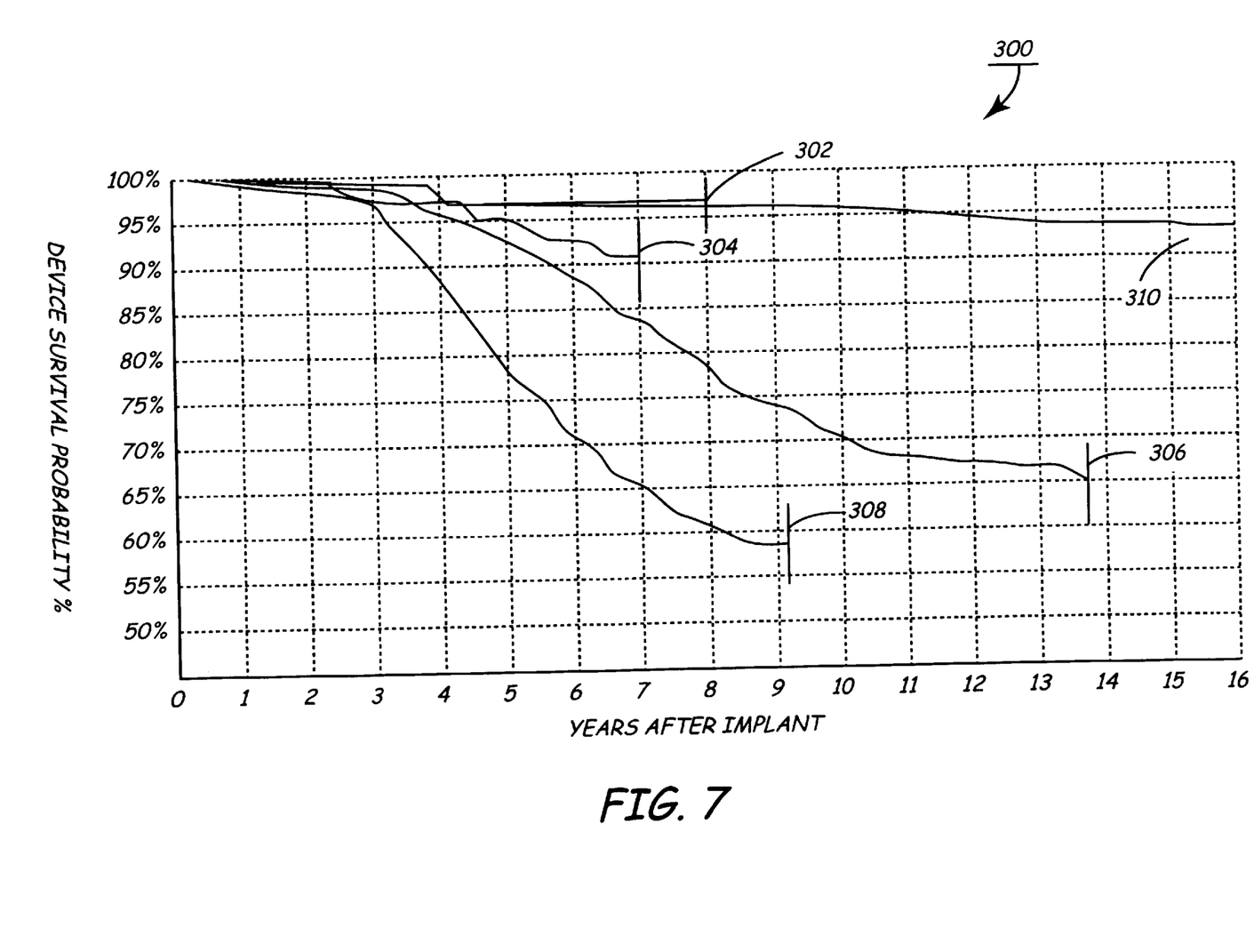
FIG. 7 is a lead survivability probability projection in accordance with the present invention.
Figure 8:
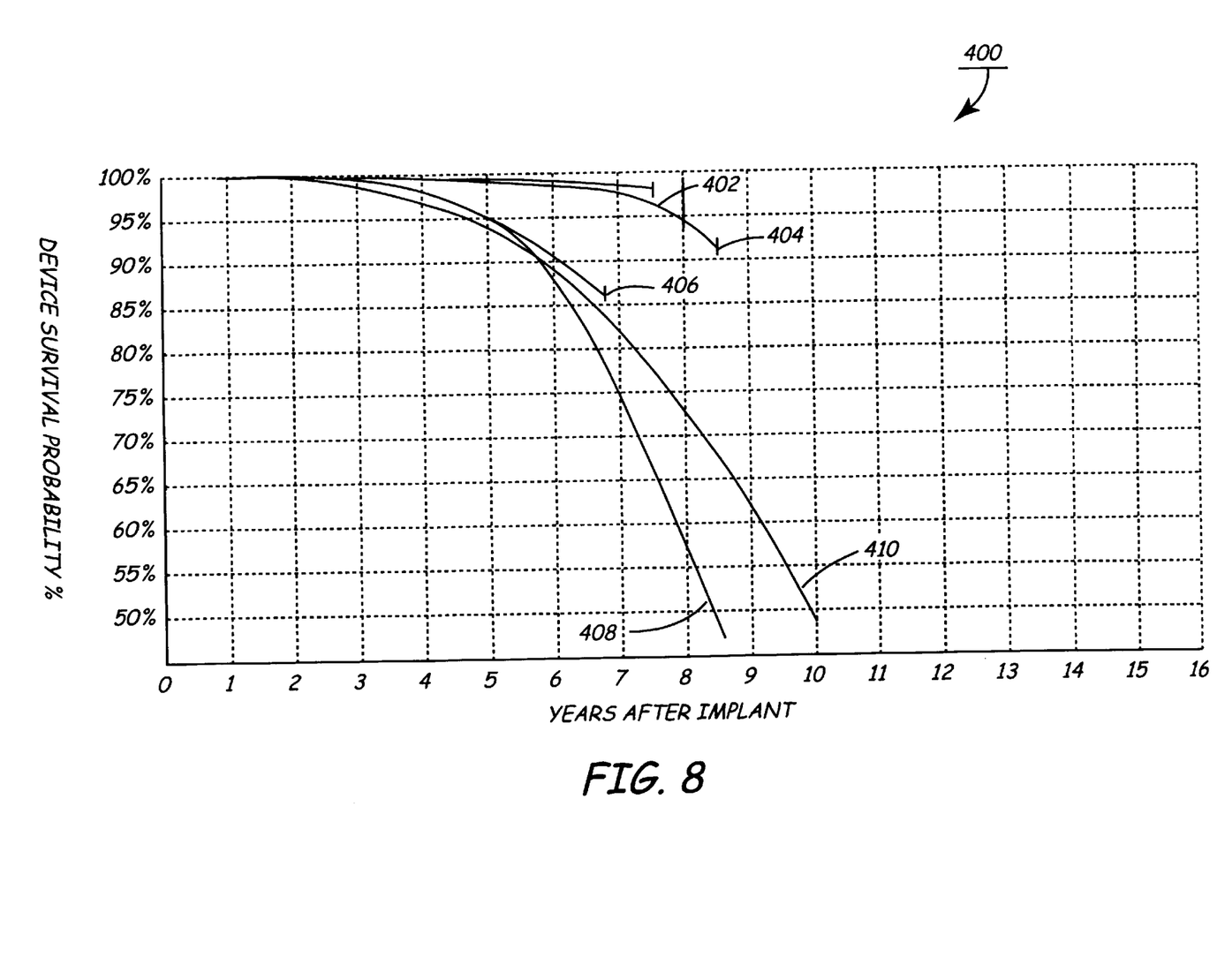
FIG. 8 is a pacemaker survivability probability projection in accordance with the present invention.

FIGS. 7 and 8 show an example of the device survival probability percent versus years after implant of various leads 300 and pacemakers 400, respectively. Plots 302, 304, 306, 308 and 310 are representative obsolete bipolar leads based on lead complications in a chronic lead study. Error bars represent 2 standard errors at the leading 6-month interval. Survival probability refers to the continued proper function of a lead type. For example, at 16 years post implant, lead 310 would have a 93% survival probability (or alternatively, each patient would have a 7% risk of incurring a lead failure and/or complication).

Plots 402, 404, 406, 408 and 410 are representative obsolete dual chamber pacemakers based on returned product analysis. Error bars represent 2 standard errors at the leading 3-month interval. Survival probability refers to the continued proper function of a device type. For example, at 10 years post implant, pacemaker 410 would have a 49% survival probability (or alternatively, each patient would have a 51% risk of incurring a pacemaker normal battery depletion, failure and/or complication).

Accordingly, the present invention provides inter alia, a system of notification of recalls and alerts, recommendations for enhanced device longevity, and recommendations for improved patient benefit and safety for IMDs via programmers or IMUs worldwide. Generally, in the context of the invention, all programmers or IMUs located proximate to IMDs or patients with IMDs and distributed globally are connected to an expert data center to share software upgrades and access archived data. The programmer or IMU function as an interface between the remotely located expert data center and the IMDs. Further, procedural functions such as monitoring the performance of the IMDs, upkeep and maintenance of the IMDs, recommendations for the programming of parameters of IMDs, prophaylactic replacement of IMDs, recommendations on the frequency of follow-up and other actions related to the patient as needed are implemented via reports to the Physician, or healthcare professional via the programmer or the IMU. Further, a physician at a remote station is preferably wirelessly linked to the remote expert data center. This scheme enables the optimization of patient care and IMD function by physicians worldwide while maintaining a high standard of patient care at reduced costs.

Although specific embodiments of the invention have been set forth herein in some detail, it is understood that this has been done for the purposes of illustration only and is not to be taken as a limitation on the scope of the invention as defined in the appended claims. It is to be understood that various alterations, substitutions, and modifications may be made to the embodiment described herein without departing from the spirit and scope of the appended claims.

What is claimed is:

1. An integrated bi-directional data communication and follow-up system far an implantable medical device (IMD) having a memory that stores device information, operational parameters including stored diagnostic data, physiological and medical data, and performance logs including battery status, the system comprising:

a remote expert station;
an external interface device in wireless data communication with the IMD and the remote expert station, the external Interface device including a data management system to enable data transfer and exchange between the IMD and the remote expert station;
a network enabling bi-directional communication between the IMD, said external interface device and said remote expert station;
means for reviewing said performance logs including battery status by comparing them to limits for the particular IMD and determining a projection of remaining IMD longevity in view of stored diagnostic data retrieved from the IMD; and
means for generating a recommendation for enhanced device longevity; and
wherein said means for reviewing performance log and said means for generating a recommendation for enhanced device longevity are implemented in one of said external interface device and said remote export station.

2. The system of claim 1 wherein said device data includes data relating to initial implant.

3. The system of claim 1 wherein said performance logs are reviewed by said means for reviewing on a periodic basis.

4. The system of claim 1 wherein said data management system includes statistical survival probability projection data based on the population of implanted medical devices related to the IMD.

5. The system of claim 4 wherein said data management system uses the projection date to generate an implanted medical device safety and performance data set and wherein said data management, system compares said performance logs against said generated performance data set.

6. The system of claim 5 wherein said data set is implemented to identify whether the IMD is out of specification.

7. The system of claim 1 wherein said means for updating includes upgrading/reprogramming the at least one IMD.

* * * * *

UNITED STATES PATENT AND TRADEMARK OFFICE
CERTIFICATE OF CORRECTION

PATENT NO. : 6,648,823 B2
DATED : November 18, 2003
INVENTOR(S) : David L. Thompson It is certified that error appears in the above-identified patent and that said Letters Patent is hereby corrected as shown below:

<u>Column 18,</u>
Line 48, "...Interface" should read -- interface --
Line 65, "export station" should read -- expert station --

Signed and Sealed this

Eighteenth Day of May, 2004

JON W. DUDAS
*Acting Director of the United States Patent and Trademark Office*